United States Patent
Taneja et al.

(10) Patent No.: US 6,692,944 B2
(45) Date of Patent: Feb. 17, 2004

(54) CHEMO-ENZYMATIC SYNTHESIS OF OPTICALLY ENRICHED ROSE-OXIDES

(76) Inventors: Shubash Chandra Taneja, Regiona Research Laboratory (Jammu), Jammu, Jammu & Kashmir (IN); Vijay Kumar Sethi, Regional Research Laboratory (Jammu), Jammu, Jammu & Kashmir (IN); Surrinder Koul, Regional Research Laboratory (Jammu), Jammu, Jammu & Kashmir (IN); Samar Singh Andotra, Regional Research Laboratory (Jammu), Jammu, Jammu & Kashmir (IN); Ghulam Nabi Qazi, Regional Research Laboratory (Jammu), Jammu, Jammu & Kashmir (IN)

( * ) Notice: Subject to any disclaimer, the term of this patent is extended or adjusted under 35 U.S.C. 154(b) by 0 days.

(21) Appl. No.: 10/109,369

(22) Filed: Mar. 29, 2002

(65) Prior Publication Data

US 2003/0186395 A1 Oct. 2, 2003

(51) Int. Cl.⁷ .................... C12P 17/06; C12N 9/14; C12N 9/20
(52) U.S. Cl. ............ 435/125; 435/195; 435/198; 435/280; 549/356
(58) Field of Search .................. 435/125, 195, 435/198, 280; 549/356

(56) References Cited

U.S. PATENT DOCUMENTS

| | | | | |
|---|---|---|---|---|
| 4,312,717 A | * | 1/1982 | Suzukamo et al. | 205/452 |
| 4,340,544 A | * | 7/1982 | Suzukamo et al. | 549/356 |
| 4,429,139 A | * | 1/1984 | Fehr | 549/356 |
| 5,672,783 A | * | 9/1997 | Matsuda et al. | 549/356 |

OTHER PUBLICATIONS http://www.mallchem.com/msds/englishhtml/A3004.htm Amberlite IR–120 data sheet.*

* cited by examiner

*Primary Examiner*—Herbert J Lilling
(74) *Attorney, Agent, or Firm*—Sughrue Mion, PLLC

(57) ABSTRACT

The present invention relates to a process for the systhesis of optically enriched dextro- and laevo-rotatory isomers of rose oxide from racemic citronellol. The invention particularly relates to the preparation of optically enriched (−)-(2 S, 4 R)-rose oxide and its isomer (+)-(2 R, 4 S)-rose oxide torn racemic citronellol.

31 Claims, No Drawings

CHEMO-ENZYMATIC SYNTHESIS OF OPTICALLY ENRICHED ROSE-OXIDES

FIELD OF THE INVENTION

The present invention relates to a process for the systhesis of optically enriched dextro- and laevo-rotatory isomers of rose oxide from racemic citronellol. The invention particularly relates to the preparation of optically enriched (−)-(2 S, 4 R)-rose oxide and its isomer (+)-(2 R, 4 S)-rose oxide from racemic citronellol.

BACKGROUND OF THE INVENTION

Natural rose oxide, a minor though essential olfactive, organoleptic constituent of Bulgarian rose and Geranium bourbon oils consists of mainly (−)-(2 S, 4 R)-2-(2-methyl-1-propenyl)-4-methyl tetrahydropyran. Natural rose oxide is a mixture of both cis- and trans-rose oxides wherein the cis-isomer is the major component. Rose oxides were first isolated from rose oil [Seidel and Stoll, Helv. Chem. Acta. 42, 1830, (1959)]. It was later found to be also an essential constituent of oil of Geranium bourbon [Seidel et al, Helv. Chem. Acta. 44, 598 (1961)].

Rose oxide is normally manufactured from citronellol which occurs in *Java citronella* oil. *Java citronella* is abundantly available raw material and its oil has significant industrial application in perfumery. Synthetically racemic citronellol is made from nerol/geraniol or citral by their hydrogenation. These monoterpenes are abundantly available from the natural sources. An elegant and economically feasible synthesis of racemic citronellol starts from dihydromyrcene (3,7-dimethyl-octa-1,6-diene) which can be obtained from the readily available α-or β-pinenes via hydrogenation and subsequent pyrolysis.

Although there are numerous ways to synthesize rose oxides, most of the presently known routes involve acid-catalysed cyclisation of (E)-3,7-dimethyl-5-octen-1,7-diol produced in various ways from citronellol [Ohloff G and Lienhard, Helv. Chem. Acta. 48, 182 (1962)]. Ohloff prepared (E)-3,7-dimethyl-5-octen-1,7-diol by the photosensitized air oxidation of citronellol to give alkyl hydroperoxide which on reduction and subsequent cyclisation with an acid gave a mixture of cis- and trans-rose oxide. Eschinasi prepared [Eschinasi E. H., J. Org. Chem. 35, 1097 (1970)] rose oxide mixture by the acid-catalysed cyclisation of (E)-8-acetoxy-2,6-dimethyl-1,3-octadiene obtained from the pyrolysis of 2,6-dimethyl-2,3,8-triacetoxy octane.

In 1984, a total synthesis of cis-rich (2S, 4 R)-rose oxide was carried out by P. Audin, et.al using chiral catalysts which is more of an academic interest [Audin, P; Douthean, A; Gore, J; Bull. Soc. Chem. Fr. 1984, 7, D-297-II 306].

No prior art is available in the literature concerning the preparation of optically enriched dextro- and laevo-rotatory isomers of rose oxides from racemic citronellol using biocatalytic methods.

OBJECTS OF THE INVENTION

The main object of the present invention, therefore, is to provide a novel synthetic process for the preparation of optically enriched (−)-(2S, 4R) and (+)-(2 R, 4 S)-rose oxides making use of a biocatalyst or a micro organism during the intermediate stage of synthesis.

Another object of the present invention is to develop a novel, economical and environment friendly process for the preparation of optically enriched rose oxide using biocatalyst or an enzyme, from racemic citronellol which is an abundantly available raw material.

SUMMARY OF THE INVENTION

Accordingly, the present invention provides a process for the preparation of optically enriched (−)-(2 S, 4 R)-rose oxide and its isomer (+)-(2 R, 4 S)-rose oxide from racemic citronellol, said process comprising cohalogenating racemic citronellol with a halogenation reagent in anhydrous alcohol to obtain an alkoxy halide, dehydrohalogenating the alkoxy halide to obtain the corresponding 3-octenol derivative, acylating the alcoholic function of the 3-octanol derivative with an acylating agent in presence of a base to give the corresponding acylate, subjecting the acylate so obtained to kinetic resolution using a biocatalyst or an enzyme, separating the mixture of reaction products comprising of optically enriched hydrolysed alcohol and unhydrolysed acylate derivatives, hydrolysing the optically enriched acylate with a base to furnish optically enriched primary alcohol and cyclised the alcohol so obtained with an acid catalyst to produce dextrorotatory (2R, 4S)-rose oxide, the optically enriched hydrolysed alcohol being directly cyclised with an acid catalyst to produce laevorotatory (2R, 4S)-rose oxide.

In on embodiment of the invention, the alkyl group in the alkoxy halide is selected from the group consisting of methyl, ethyl, n-propyl and n-butyl.

In another embodiment of the invention, the halide is selected from the group consisting of chloro-, bromo-, iodo-.

In another embodiment of the invention, the 3-octanol formed is 2-alkoxy-3-halo-2,6-dimethyl-8-octanol.

In another embodiment of the invention, dehydrohalogenation of the alkoxy halide is done using a strong base or an alkali to provide (E)-2-alkoxy-2,6-dimethyl-3-octen-8-ol.

In a further embodiment of the invention, (E)-2-alkoxy-2,6-dimethyl-3-octen-8-ol is acylated to obtain (E)-8-acyloxy-2-alkoxy-2,6-dimethyl-3-octene.

In another embodiment of the invention, cohalogenation of racemic citronellol is carried out using an N-halogenated succinimide selected from the group consisting of N-chlorosucccinimide, N-bromosuccinimide and N-iodosuccinimide.

In another embodiment of the invention, cohalogenation of the racemic citronellol is done using a halogen selected from bromine and iodine, or a halogenated salt selected from iodine mono chloride and potassium iodate.

In another embodiment of the invention, the cohalogenation of the racemic citronellol is carried out in a polar anhydrous alcoholic solvent selected from the group consisting of methanol, ethanol and propanol.

In a further embodiment of the invention, the cohalogenation of the racemic citronellol is effected at a temperature at 0–50° C., more preferably at 10–20° C.

In another embodiment of the invention, the base used dehydrohalogenation of the alkoxy halide is an inorganic base selected from the group comprising sodium hydroxide, potassium hydroxide and barium hydroxide.

In yet another embodiment of the invention, the base used for dehydrohalogenation of the alkoxy halide is an organic base selected from the group consisting of dimethyl amine, triethyl amine, 1,8-diazabicyclo [5,4,0] undec-7-ene and pyridine.

In yet another embodiment of the invention, the acylating agent is selected from an acid anhydride and an acylchloride.

In a further embodiment of the invention, the acid anhydride is selected from the group consisting of acetic anhydride, propanoic anhydride and butanoic anhydride.

In a further embodiment of the invention, the acylchloride is selected from acetyl chloride and propanoyl chloride.

In yet another embodiment of the invention, the acylation is carried out in the presence of an organic base selected from the group consisting of pyridine, 4-dimethyl amino pyridine and piperidine, preferably pyridine.

In yet another embodiment of the invention, the enzyme catalyst is selected from a hydolase and lipase selected from Pseudomonas sp lipase (PSL) and *Candide cylinderacae* lipase (CCL).

In another embodiment of the invention the acylation is carried out in an aqueous or phosphate buffer, with the pH of the aqueous medium being maintained at pH 5–9, more preferably at 7.

In another embodiment of the invention, the temperature of the enzymatic reaction is maintained at a range of 10–45° C., preferably at a range of 15–20° C.

In yet another embodiment of the invention, separation of optically enriched unhydrolysed acylate and hydrolysed primary alcohol is effected by column chromatography or fractional distillation.

In yet another embodiment of the invention, the deacetylation of the optically enriched acylate to produce optically enriched alcohol is carried out using an alcoholic or aqueous solution of a base selected from the group consisting of sodium carbonate, sodium hydroxide, potassium hydroxide and barium hydroxide, preferably sodium hydroxide.

In yet another embodiment of the invention, the cyclisation of optically enriched dextrorotatory and laevorotatory alcohol is carried out using an acidic reagent selected from a strongly acidic resin and a dilute mineral acid.

In a further embodiment of the invention, the dilute mineral acid is selected from the group consisting of hydrochloric acid, sulphuric acid and phosphoric acid.

In yet another embodiment of the invention, the acid resin is "AMBERLITE JR-120" available from Aldrich Chemical Co., Inc. of Milwaukee Wis. which is a sulfonated divinylbenzene/styrene copolymer, Na ion form that is a strongly acidic cation exchange resin.

DETAILED DESCRIPTION OF THE INVENTION

The invention provides a process for the preparation of optically enriched (−)-(2 S, 4 R)-rose oxide and its isomer (+)-(2 R, 4 S)-rose oxide from racemic citronellol which comprises cohalogenation reaction of racemic citronellol with a halogenating reagent in an anhydrous alcoholic solvent to produce racemic alkoxy halide wherein the alkyl group is either of methyl, ethyl, n-propyl and n-butyl and the like and the halogen is chloro-, bromo-, iodo-. Subsequently, the alkoxy halide obtained is dehydrohalogenated by a base or an alkali to furnish the corresponding 3-octenol derivative. The alcoholic function of the 3-octanol derivative is then acylated with an acylating agent in presence of a base to give the corresponding acylate, which is then reacted with a biocatalyst or an enzyme. The reaction product mixture comprising of optically enriched hydrolysed alcohol and unhydrolysed acylate derivatives. The optically enriched acylate is hydrolysed with a base to furnish optically enriched primary alcohol and then cyclised with an acid catalyst to produce dextrorotatory (2R, 4S)-rose oxide. The optically enriched hydrolysed alcohol is directly cyclised with an acid catalyst to produce laevorotatory (2R, 4S)-rose oxide.

Cohalogenation of racemic citronellol is effected either by N-halogenated succinimide selected from N-chlorosuccinimide, N-bromosuccinimide, N-iodosuccinimide or a halogen or halogenated salts such as bromine, iodine, iodine mono chloride, potassium iodate and the like but more preferably N-halogenated succinimide and most preferably N-bromo succinimide in a polar anhydrous alcoholic solvent such as methanol, ethanol, propanol and the like but more preferably methanol. Cohalogenation is effected at a temperature at 0–50° C., more preferably at 10–20° C. The base used for dehydrohalogenation of the halogenated product may be selected from inorganic bases such as sodium hydroxide, potassium hydroxide or barium hydroxide or it may be selected from the organic bases such as dimethyl amine, triethyl amine, DBU (1,8-diazabicyclo [5,4,0] undec-7-ene), pyridine and the like but more preferably an organic base to produce (E)-2-alkoxy-2,6-dimethyl-3-octan-8-ol.

The acylation of the racemic compound is carried out using an acetylating agent such as acid anhydride or acylchlorides selected from acetic anhydride, propanoic anhydride, butanoic anhydride and the like or acetyl chloride, propanoyl chloride and the like, more preferably acetic anhydride in presence of an organic base such as pyridine, 4-dimethyl amino pyridine, piperidine and the like but preferably pyridine. The racemic acylate is reacted with a biocatalyst or an enzyme like hydrolase, lipase such as Pseudomonas sp lipase (PSL)., Candide cylinderacae lipase (CCL), in an aqueous or phosphate buffer. The pH of the aqueous medium is maintained at pH 5–9, more preferably at 7. The temperature during the enzymatic reaction is maintained at 10–45° C. but more preferably at 15–20° C. Separation of optically enriched unhydrolysed acylate and hydrolysed primary alcohol respectively, is affected by column chromatography or factional distillation. The deacetylation of the optically enriched acylate to produce optically enriched alcohol is performed by an alcoholic or aqueous solution of a base such as sodium carbonate, sodium hydroxide, potassium hydroxide, barium hydroxide and the like, but more preferably sodium hydroxide. The cyclisation of optically enriched dextrorotatory and laevorotatory alcohols is performed using acidic reagents such as a strongly acidic resin or a dilute mineral acid such as hydrocholoric acid, sulphuric acid, phosphoric acid and the like but more preferably a resin such as "AMBERLITE IR-120" plus in aqueous or aqueous alcoholic solution at a temperature 0-40° C., more preferably 10° C.

The invention is described herein with reference to the examples given below. These examples should not be construed as to restrict the scope of this invention

EXAMPLE I

Step-1: Synthesis of (±)-3-bromo-2-methoxy-2,6-dimethyl-octan-8-ol

N-bromosuccinimide (60.0 g, 0.337 mole) is dissolved in methanol (500 ml) in a flask fitted with a thermometer, a dropping funnel and a nitrogen inlet. Citronellol (50.0 g, 0.32 mole) is placed in a dropping funnel and added slowly with vigorous stirring at a temperature of 15–20° C. in nitrogen atmosphere. The temperature during the addition of citronellol is maintained between 18–20° C. After the reaction is complete, the reaction mixture is poured in water in a separating funnel and extracted with n-hexane (3×100 ml). The n-hexane extract is washed with 5% sodium carbonate solution (2×100 ml) and then with water (2×200 ml). Finally, the solvent layer is dried over anhydrous sodium sulphate and concentrated to give a colourless oil of compound of formula 3 (77.0 g, 90%).

Step-2: Preparation of (±)-2-methoxy-2,6-dimethyl-3-octen-8-ol 3-bromo-2-methoxy-2,6-dimethyl-octan-8-ol (50.0 g, 0.187 moles) is dissolved in methanol (500 ml) in a flask fitted with a condenser. Sodium hydroxide (20 g) is added in the flask and the reaction mixture refluxed on the water bath for six hrs. After the reaction is complete, solvent is removed by distillation at reduced pressure bringing the total volume to one-fourth. The reaction contents are then poured in water in a separating funnel and extracted with chloroform (3×100 ml). The solvent layer is washed with water (2×100 ml) to neutral pH. Finally chloroform layer is dried over anhydrous calcium chloride and concentrated under vacuo to give a colourless oily substance which is identified as 2-methoxy-2,6-dimethyl-3-octen-8-ol of formula 4 by spectral methods, (30.1 g, 86%).

Step-3: Preparation of (±)8-acetoxy-2-methoxy-2,6-dimethyl-3-octene

A mixture of 2-methoxy-2,6-dimethyl-3-octen-8-ol (10 g, 0.053 mole), fleshly distilled acetic anhydride (30 ml), and dry pyridne (3 ml) is kept at room temp. for 8 hr. The reaction mix is then poured over ice water and extracted with ethyl acetate (3×50 ml). The solvent layer is first extracted with dilute hydrochloric acid (10%, 15 ml) and then washed with water to neutral pH and finally dried over anhydrous sodium sulphate and concentrated to give an oily substance identified as 8-acetoxy-2-methoxy-2,6-dimethyl-3-octene by spectral data, (11.0 g, 90%).

Step-4: Enzymatic Preparation of 1-(−)2-methoxy-2,6-dimethyl-3-octen-8-ol and d-(±)-8-acetoxy-2-methoxy-2,6-dimethyl-3-octene.

8-acetoxy-2-methoxy-2,6-dimethyl-3-octene (10.0 g, 43 mmole) is suspended in buffer phosphate (40 ml) at pH 7.0–7.3 in a round bottom flask and to this added the enzyme powder Pseudomonas sp. Lipase (PSL) (200 mg) with continuous stirring at 250–300 rpm for 24 hrs. The reaction is then stopped and the contents extracted wit chloroform (3×50 ml). The organic layer is washed with water (2×50 ml), dried over anhydrous sodium sulphate and concentrated under vacuum to give an oil (8.1 g) comprising a mixture of unhydrolysed and hydrolysed products. This mixture is separated over a silica gel column and oil elution with hexane:ethyl acetate (95.:5 to 80:20) with gradient elution to furnish oil 1-(−)-2-methoxy-2,6-dimethyl-3-octen-8-ol (5.1 g) and other oily substance d-(+)-8-acetoxy-2-methoxy-2,6-dimethyl-3-octene (2.7 g) respectively which are identified by spectral means.

Step-5: Preparation of d-(+)-2-methoxy-2,6-dimethyl-3-octen-8-ol.

The compound d-(+)-8-acetoxy-2-methoxy-2,6-dimethyl-3-octene (2.6 g, 11.4 mmole) is dissolved in methanol (30 ml) and to this is added potassium hydroxide (1.5 g) and refluxed on a water both for 1 hr. Methanol is then removed by distillation under reduced pressure and reaction product dissolved in solvent ether (50 ml), solvent layer is washed with water, dried over anhydrous sodium sulphate and evaporated at reduced pressure to give an oily substance identified as d-(+)-2-methoxy-2,6-dimethyl-3-octen-8-ol by spectral data (2.0 g. 94%).

Step-6: Preparation of 1-(−)-rose oxide 1-(−)-2-methoxy-2,6-dimethyl-3-octen-8-ol (5 g, 26.8 mmole) was dissolved in acetone (50 ml) in a round bottom flask. The resin "AMBERLITE IR-120" plus (3 g) is added and the mixture is stirred at room temperature for 8 hrs. After the completion of reaction the resin is removed by filtration and the solvent layer washed with water. The solvent is removed in vacuo. The crude product thus obtained is distilled in vacuo at reduced pressure to produce the cyclised product I-(−)-rose oxide (3.6 g, 86.9%); $[\alpha]^{26}_D$-12° (neat), cis: trans (85:15) by glc.

Step-7: Preparation of d-(+)-rose oxide.

The compound d-(+)-2-methoxy-2,6-dimethyl-3-octen-8-ol (2.0 g, 10.75 mmole) is cyclised by the resin Amberlite IR-120 plus (2.0 g) as discussed above (step 6) to furnish d-(+)-rose oxide (1.4 g, 84, 8%); $[\alpha]^{26}_D$+31° (neat) cis:tans (85:15) by glc.

EXAMPLE-2

Step-1: Synthesis of (±)-3-iodo-2-ethoxy-2,6-dimethyloctan-8-ol.

Iodine monochloride (55.0 g, 0.34 mole) is taken in methanol (500 ml) in a flask fitted with a thermometer, a dropping funnel and a nitrogen inlet. Citronellol (55.0 g, 0.34 mole) is taken in the dropping funnel and added slowly with vigorous sirring at a temperature of 10° C. and nitrogen gas is purged in the reaction flask. After the addition of citronellol has been completed, the reaction mixture is maintained at a temperature around 10–15° C. for 5 hrs. The stirring is stopped and the reaction mixture is poured in water in a separating funnel and extracted with n-hexane (3×100 ml). The solvent layer is washed with 5% sodium carbonate solution (2×100 ml) and then with water (2×250 ml). Finally the solvent layer is washed with water and dried over anhydrous sodium sulphate and concentrated under vacuum to give a pure light brown oil (90.2 g, 94%) identical as 3-iodo-2-ethoxy-2,6-dimethyl-8-ol.

Step-2: Preparation of (±)-2-ethoxy-2,6-dimethyl-3-octen-8-ol

The compound 3-iodo-2-ethoxy-2,6-dimethyl-octan-8-ol (50.0 g, 0.15 mole) is dissolved in methanol (500 ml) in a flask fitted with a condenser. Triethyl amine (15 ml) is added in the flask and refluxed the reaction mixture on a water bath for 10 hr. After the reaction is complete, solvent is removed by distillation at reduced pressure to bring the total volume to one fourth. The reaction mixture is then poured in dilute acid solution (10% hydrochloric acid) in a separating funnel and extracted with ethyl acetate (3×100 ml) and solvent layer is washed with water (2×100 ml ) till neutral pH. Finally the solvent layer is dried over anhydrous sodium sulphate and concentrated to give an oily substance which is identified as (±)-2-ethoxy-2,6-dimethyl-3-octen-8-ol by spectral methods (25.9 g, 85%).

Step-3: Preparation of (±)8-acetoxy-2-ethoxy-2,6-dimethyl-3octene.

A mixture of 2-ethoxy-2,6-dimethyl-3-octen-8-ol (10 g, 0.05 mole), freshly distilled acetic anhydride (30 ml) and dimethylaminopyridine (100 mg) is kept at room temperature for 24 hr. Reaction mixture is then poured into cold water (50 ml), acidified with dilute hydrochloric acid (10%) and extracted with n-hexane (3×50 ml). The hexane extract is washed with water (2×25 ml), dried over sodium sulphate and concentrated under vacuum to give an oily substance identified as (±)8-acetoxy-2-ethoxy-2,6-dimethyl-3-octene (11.2 g, 92.5%).

Step-4: Enzymatic Preparation of 1-(−)-2-ethoxy-2,6-dimethyl-3-octen-8-ol and d-(+)-8-acetoxy 2-ethoxy-2,6-dimethyl-3-octene.

The compound 8-acetoxy-2-ethoxy-2,6-dimethyl-3-octene (10.0 g, 41.3 mmole) is suspended in n-hexane (50 ml) in a round bottom and to this added the enzyme powder candida rugosa lipase (CRL) (200 mg) with continuous stirring for 24 hrs. The reaction mixture is then poured in water and extracted with solvent ether (3×100 ml). The ether layer is then washed with water, dried over anhydrous sodium sulphate and concentrated under vacuum to give an oil (8.0 g) comprising a mixture of hydrolised and unhydrolysed products. This mixture are is separated over a silica gel column with gradient elution with hexane: ethylacetate (95:5 to 80:20) with gradient elusion to finish 1-(−)-2-ethoxy-2,6-dimethyl-3-octen-8-ol (5.0 g) and other oily substance d-(+)-8-acetoxy-2-ethoxy-2,6-dimethyl-3-octene (2.6 g) which are identified by spectral data.

Step 5: Preparation of d-(+)-2-ethoxy-2,6-dimethyl-3-octen-8-ol.

The compound d-(+)-8-acetoxy-2-ethoxy-2,6-dimethyl-3-octene (2.6 g, 10.7 mmole) is dissolved in methanol (30 ml) and to this is added sodium hydroxide (2.0 g) and refluxed on a water bath for 1 h. Methanol is then removed by distillation under reduced pressure. The reaction product is then redissolved in solvent ether (50 ml), washed with water to neutral pH, dried over anhydrous sodium sulphate and concentrated to give an oily substance identified as d-(+)-2-ethoxy-2,6-dimethyl-3-octen-8-ol, the structure of which is confirmed by spectral data (2.0 g, 94%).

Step-6: Preparation of 1-(−)-rose oxide

The compound 1-(−)-2-ethoxy-2,6-dimethyl-3-octen-8-ol (5.0 g, 25 mmole) was dissolved in acetone (100 ml) in a round bottom flask and to this added a mixture of acetic acid-sulphuric acid (9:1, 3 ml) at 0° and stirred the solution for 5 hr After the completion of the reaction the reaction product is poured over water and extracted with solvent ether. The solvent layer is then washed with water to neutral pH and dried over anhydrous sodium sulphate. The solvent is removed under vacuum. The crude product thus obtained is purified over a silica gel column with gradient elution using hexane:ethyl acetate mixture (95:5 to 90:10) as eluents. The oily substance thus obtained is identified as 1-(−)-rose oxide by spectral studies (3.35 g, 87%)[α]$_D^{26}$−35° (CHCl$_3$, c 1.0)

Step-7: Preparation of d-(+)-rose oxide

The compound d-(+)-2-ethoxy-2,6-dimethyl-3-octen-8-ol (2.0 g, 10 mmole) is cyclised by acetic acid-sulphuric acid mixture (9:1) as discussed in step 6 to give d-(+)-rose oxide (1.45 g, 87.8%), [α]$_D^{26}$+17 (CHCl$_3$ c 1.0).

Advantages

1. The process utilises raciemic citronellol which is a cheap raw material.
2. The process provides a chemo-enzymatic methodology not known earlier.
3. The total yield of the final products are high.
4. The process provides predotninantly cis-rose oxides,
5. The process gives high optical enrichment of the desired products.

We claim:

1. A process for the preparation of optically enriched (−)-(2 S, 4 R)-rose oxide and its isomer (+)-(2 R, 4 S)-rose oxide from racemic citronellol, said process comprising cohalogenating racemic citronellol with a halogenation reagent in anhydrous alcohol to obtain an alkoxy halide, dehydrohalogenating the alkoxy halide to obtain the corresponding 3-octenol derivative, acylating the alcoholic function of the 3-octanol derivative with an acylating agent in presence of a base to give the corresponding acylate, subjecting the acylate so obtained to kinetic resolution using a biocatalyst or an enzyme, separating the mixture of reaction products comprising of optically enriched hydrolysed alcohol and unhydrolysed acylate derivatives, hydrolysing the optically enriched acylate with a base to furnish optically enriched primary alcohol and cyclised the alcohol so obtained with an acid catalyst to produce dextrorotatory (2R, 4S)-rose oxide, the optically enriched hydrolysed alcohol being directly cyclised with an acid catalyst to produce laevorotatoty (2R, 4S)-rose oxide.

2. A process as claimed in claim 1 wherein the alkyl group in the alkoxy halide is selected from the group consisting of methyl, ethyl, n-propyl and n-butyl.

3. A process as claimed in claim 1 wherein the halide is selected from the group consisting of chloro-, bromo-, iodo-.

4. A process as claimed in claim 1 wherein the 3-octanol formed is 2-alkoxy-3-halo-2,6-dimethyl-8-octanol.

5. A process as claimed in claim 1 wherein the dehydrohalogenation of the alkoxy halide is done using a strong base or an alkali to provide (E)-2-alkoxy-2,6-dimethyl-3-octen-8-ol.

6. A process as claimed in claim 5 wherein the (E)-2-alkoxy-2,6-dimethyl-3-octen-8-ol is acylated to obtain (E)-8-acyloxy-2-alkoxy-2,6-dimethyl-3-octene.

7. A process as claimed in claim 1 wherein the cohalogenation of racemic citronellol is carried out using an N-halogenated succinimide selected from the group consisting of N-chlorosuccinimide, N-bromosuccinimide and N-iodosuccinimide.

8. A process as claimed in claim 1 wherein the cohalogenation of the racemic citronellol is done using a halogen selected from bromine and iodine, or a halogenated salt selected from iodine mono chloride and potassium iodate.

9. A process as claimed in claim 1 wherein the cohalogenation of the racemic citronellol is carried out in a polar anhydrous alcoholic solvent selected from the group consisting of methanol, ethanol and propanol.

10. A process as claimed in claim 1 wherein the cohalogenation of the racemic citronellol is effected at a temperature in the range of 0–50° C.

11. A process as claimed in claim 10 wherein the cohalogenation of the racemic citronellol is effected at a temperature in the range of 10–20° C.

12. A process as claimed in claim 1 wherein the base used for dehydrohalogenation of the alkoxy halide is an inorganic base is selected from the group comprising sodium hydroxide, potassium hydroxide and barium hydroxide.

13. A process as claimed in claim 1 wherein the base used for dehydrohalogenation of the alkoxy halide is an organic base selected from the group consisting of dimethyl amine, triethyl amine, 1,8-diazabicyclo [5,4,0] undec-7-ene and pyridine.

14. A process as claimed in claim 1 wherein the acylating agent is selected from an acid anhydride and an acylchloride.

15. A process as claimed in claim 14 wherein the acid anhydride is selected from the group consisting of acetic anhydride, propanoic anhydride and butanoic anhydride.

16. A process as claimed in claim 14 wherein the acylchloride is selected from acetyl chloride and propanoyl chloride.

17. A process as claimed in claim 1 wherein the acylation is carried out in the presence of an organic base selected from the group consisting of pyridine, 4-dimethyl amino pyridine and piperidine.

18. A process as claimed in claim 17 wherein the organic base is pyridine.

19. A process as claimed in claim 1 wherein the enzyme catalyst is selected from a hydrolase and lipase selected from Pseudomonas sp lipase and *Candide cylinderacae* lipase.

20. A process as claimed in claim 1 wherein the acylation is carried out in an aqueous or phosphate buffer, with the pH of the aqueous medium being maintained at pH 5–9.

21. A process as claimed in claim 20 wherein the pH of the aqueous medium is 7.

22. A process as claimed in claim 1 wherein the temperature of the enzymatic reaction is maintained at 10–45° C.

23. A process as claimed in claim 1 wherein the temperature of the enzymatic reaction is maintained at 15–20° C.

24. A process as claimed in claim 1 wherein the separation of optically enriched unhydrolysed acylate and hydrolysed primary alcohol is effected by column chromatography or fractional distillation.

25. A process as claimed in claim 1 wherein the deacetylation of the optically enriched acylate to produce optically enriched alcohol is carried out using an alcoholic or aqueous solution of a base selected from the group consisting of sodium carbonate, sodium hydroxide, potassium hydroxide and barium hydroxide.

26. A process as claimed in claim 25 wherein the base is sodium hydroxide.

27. A process as claimed in claim 1 wherein the cyclisation of optically enriched dextrorotatory and laevorotatory alcohol is carried out using an acidic reagent selected from a strongly acidic resin and a dilute mineral acid.

28. A process as claimed in claim 27 wherein the dilute mineral acid is selected from the group consisting of hydrochloric acid, sulphuric acid and phosphoric acid.

29. A process as claimed in claim 27 wherein the acid resin comprises a sulfonated divinylbenzene/styrene copolymer, Na form that is a strongly acidic cation exchange resin.

30. A process as claimed in claim 1 wherein the cyclisation is carried out in an aqueous or aqueous alcoholic solution at a temperature in the range of 0–40° C.

31. A process as claimed in claim 30 wherein the cyclisation is carried out in an aqueous or aqueous alcoholic solution at a temperature of 10° C.

\* \* \* \* \*